United States Patent [19]
Sherman et al.

[11] Patent Number: 6,124,262
[45] Date of Patent: Sep. 26, 2000

[54] COMPOSITIONS AND METHODS FOR REDUCING ADHESIVENESS OF DEFECTIVE RED BLOOD CELLS

[75] Inventors: Irwin William Sherman; Ian Edward Crandall, both of Riverside; Stephen Byron Shohet; Bernard Jean-Marie Thévenin, both of San Francisco, all of Calif.

[73] Assignee: The Regents of the University of California, Oakland, Calif.

[21] Appl. No.: 08/405,647

[22] Filed: Mar. 17, 1995

[51] Int. Cl.$^7$ .............................. A61K 38/00; C07K 5/00
[52] U.S. Cl. ................................. 514/15; 514/12; 514/14; 514/17; 530/324; 530/326; 530/327; 530/328; 530/329
[58] Field of Search ............................ 530/324, 326–329; 514/12, 14–17

[56] References Cited

U.S. PATENT DOCUMENTS 5,157,620  10/1992  Kay et al. ................................... 514/13
5,861,243   1/1999  Dietrich et al. ............................. 435/5

FOREIGN PATENT DOCUMENTS 39 34 366 A1  4/1991  Denmark ........................ A61K 39/42
92/19646     11/1992  WIPO .
WO 93/19085   9/1993  WIPO .............................. C07K 3/12

OTHER PUBLICATIONS

Lux, et al, Proc. Natl. Acad. Sci, vol. 86, pp. 9089–9093, 1989.
Hebbel, et al, J. Clincal Investigation, vol. 65, 1980, 154–160.
Tanner et al, Biochem. J., vol. 256, pp. 703–712.
Crandall et al, Parasitology (1994), 108 (4), 389–96.
Winograd et al, J. Cell Biol., v. 108, pp. 23–30, 1989.
Kaul et al, Proc. Natl. Acad. Sci USA, vol. 86, pp. 3356–3360, 1989.
CAPLUS Abstracts No. 1993:642318 and 1993:248879 to Wu et al. and Hatfull et al., 1993.
I. Crandall and I.W. Sherman, "The human anion transport protein, band 3, contains a CD36–like binding domain for *Plasmodium falciparum*–infected erythrocytes" *Parasitology* 112:261–267 (1996).
Crandall et al., "Synthetic peptides based on motifs present in human band 3 protein inhibit cytoadherence/sequestration of the malaria parasite *Plasmodium falciparum*" *Proc. Natl. Acad. Sci. USA* 90:4703–4707 (1993).
Hogh et al., "Immune Responses to Band 3 Neoantigens on *Plasmodium falciparum*–Infected Erythrocytes in Subjects Living in an Area of Intense Malaria Transmission Are Associated with Low Parasite Density and High Hematocrit Value" *Infection and Immunity* 62(10):4362–4366 (1994).
Chappey, et al., "Adhesion of erythrocytes to endothelium in pathological situations: a review article" *Nouv. Rev. Fr. Hematol.* 36:281–288 (1994).
Puyal, et al., "Design of a short membrane–destabilizing peptide covalently bound to liposomes" *Biochimica et Biophysica Acta* 1195:259–266 (1994).

*Primary Examiner*—Bennett Celsa
*Attorney, Agent, or Firm*—Townsend and Townsend and Crew LLP

[57] ABSTRACT

Peptide sequences and analogs thereof based on amino acid motifs in band 3 which are effective in reducing the adhesiveness of pathologically adhesive red blood cells. One class of peptide sequences are characterized by the sequence motif $Z^1$xKxxx+ (SEQ ID NO:45), wherein $Z^1$ is selected from the group consisting of tyrosine, phenylalanine and alanine; x is an unobstructive residue and + is a positively charged residue (e.g., K or P—H). These peptides are used to reduce adhesiveness in the treatment of sickle cell disease, thalassemia and diabetes. A second class of peptide sequences are characterized by the sequence motif $Z^2Z^3Z^2$-x-xxxx– (SEQ ID NO:46), wherein $Z^2$ represents a hydrophobic residue, x is an unobstructive residue and – is a negatively charged residue. These peptides can be used to reduce adhesiveness in the treatment of malria, sickle cell disease, thalassemia and diabetes.

6 Claims, 5 Drawing Sheets

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

His Pro Leu Gln Lys Thr Tyr
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Tyr Val Lys Arg Val Lys
1               5

(2) INFORMATION FOR SEQ ID NO:3:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Tyr Val Lys
1

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide

```
        (xi) SEQUENCE DESCRIPTION: SEQ ID NO:4:

His Pro Gln Lys Thr Tyr
1               5

(2) INFORMATION FOR SEQ ID NO:5:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

His Pro Leu Gly Gln Lys Thr Tyr
1               5

(2) INFORMATION FOR SEQ ID NO:6:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Asp His Pro Leu Gln Lys Thr Tyr Asn Tyr
1               5                   10

(2) INFORMATION FOR SEQ ID NO:7:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Tyr Thr Gln Lys Leu Ser Val Pro Asp Gly Phe Lys Val Ser Asn
1               5                   10                  15

(2) INFORMATION FOR SEQ ID NO:8:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Lys Leu Ile Lys Ile Phe Gln Lys His Pro Leu Gln Lys Thr Tyr
1               5                   10                  15

(2) INFORMATION FOR SEQ ID NO:9:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide
```

(xi) SEQUENCE DESCRIPTION: SEQ ID NO:9:

Lys Pro Pro Lys Tyr His Pro Asp Val Pro Tyr Val Lys Arg
1               5                   10

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Asp Val Pro Tyr Val Lys Arg Val Lys Thr Trp Arg Met His
1               5                   10

(2) INFORMATION FOR SEQ ID NO:11:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Asn Tyr Asn Val Leu Met Val Pro Lys Pro Gln Gly Pro Leu Pro Asn
1               5                   10                  15

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Gly His Pro Leu Gln Lys Thr Tyr
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Tyr Thr Lys Gln Leu Pro His Gly
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear

```
       (ii) MOLECULE TYPE: peptide (xi) SEQUENCE DESCRIPTION: SEQ ID NO:14:

Lys Pro Pro Lys Tyr His Pro
1               5

(2) INFORMATION FOR SEQ ID NO:15:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:15:

Phe Val Lys Arg Val Lys Thr Tyr
1               5

(2) INFORMATION FOR SEQ ID NO:16:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:16:

Leu Tyr Pro Gln His Lys Thr
1               5

(2) INFORMATION FOR SEQ ID NO:17:

(i) SEQUENCE CHARACTERISTICS:
           (A) LENGTH: 12 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:17:

Phe Gln Asp His Pro Leu Gln Lys Thr Tyr Asn Tyr
1               5                   10

(2) INFORMATION FOR SEQ ID NO:18:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:18:

Ala Pro Leu Gln Lys Thr Tyr
1               5

(2) INFORMATION FOR SEQ ID NO:19:

(i) SEQUENCE CHARACTERISTICS:
           (A) LENGTH: 7 amino acids
           (B) TYPE: amino acid
           (C) STRANDEDNESS:
           (D) TOPOLOGY: linear
```

```
        (ii) MOLECULE TYPE: peptide (xi) SEQUENCE DESCRIPTION: SEQ ID NO:19:

His Ala Leu Gln Lys Thr Tyr
1               5

(2) INFORMATION FOR SEQ ID NO:20:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:20:

His Pro Ala Gln Lys Thr Tyr
1               5

(2) INFORMATION FOR SEQ ID NO:21:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:21:

His Pro Leu Ala Lys Thr Tyr
1               5

(2) INFORMATION FOR SEQ ID NO:22:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:22:

His Pro Leu Gln Ala Thr Tyr
1               5

(2) INFORMATION FOR SEQ ID NO:23:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:23:

His Pro Leu Gln Lys Ala Tyr
1               5

(2) INFORMATION FOR SEQ ID NO:24:

(i) SEQUENCE CHARACTERISTICS:
            (A) LENGTH: 7 amino acids
            (B) TYPE: amino acid
            (C) STRANDEDNESS:
```

```
            (D) TOPOLOGY: linear (ii) MOLECULE TYPE: peptide (xi) SEQUENCE DESCRIPTION: SEQ ID NO:24:

His Pro Leu Gln Lys Thr Ala
1               5

(2) INFORMATION FOR SEQ ID NO:25:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:25:

His Pro Leu Gly Gln Lys Thr Tyr
1               5

(2) INFORMATION FOR SEQ ID NO:26:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:26:

Phe Ser Phe Cys Glu Thr Asn Gly Leu Glu
1               5                   10

(2) INFORMATION FOR SEQ ID NO:27:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Phe Glu Thr Leu Gly Cys Asn Glu Gly Phe
1               5                   10

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:28:

Phe Phe Ser Ala Thr Leu Gly Asn Glu Glu
1               5                   10

(2) INFORMATION FOR SEQ ID NO:29:

(i) SEQUENCE CHARACTERISTICS:
            (A) LENGTH: 10 amino acids
            (B) TYPE: amino acid
```

(C) STRANDEDNESS:
            (D) TOPOLOGY: linear (ii) MOLECULE TYPE: peptide (xi) SEQUENCE DESCRIPTION: SEQ ID NO:29:

Ala Ser Phe Cys Glu Thr Asn Gly Leu Glu
1               5                   10

(2) INFORMATION FOR SEQ ID NO:30:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:30:

Phe Ala Phe Cys Glu Thr Asn Gly Leu Glu
1               5                   10

(2) INFORMATION FOR SEQ ID NO:31:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:31:

Phe Ser Ala Cys Glu Thr Asn Gly Leu Glu
1               5                   10

(2) INFORMATION FOR SEQ ID NO:32:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:32:

Phe Ser Phe Ala Glu Thr Asn Gly Leu Glu
1               5                   10

(2) INFORMATION FOR SEQ ID NO:33:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:33:

Phe Ser Phe Cys Ala Thr Asn Gly Leu Glu
1               5                   10

(2) INFORMATION FOR SEQ ID NO:34:

(i) SEQUENCE CHARACTERISTICS:
            (A) LENGTH: 10 amino acids

```
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:34:

Phe Ser Phe Cys Glu Ala Asn Gly Leu Glu
1               5                   10

(2) INFORMATION FOR SEQ ID NO:35:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:35:

Phe Ser Phe Cys Glu Thr Ala Gly Leu Glu
1               5                   10

(2) INFORMATION FOR SEQ ID NO:36:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:36:

Phe Ser Phe Cys Glu Thr Asn Ala Leu Glu
1               5                   10

(2) INFORMATION FOR SEQ ID NO:37:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:37:

Phe Ser Phe Cys Glu Thr Asn Gly Ala Glu
1               5                   10

(2) INFORMATION FOR SEQ ID NO:38:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:38:

Phe Ser Phe Cys Glu Thr Asn Gly Leu Ala
1               5                   10

(2) INFORMATION FOR SEQ ID NO:39:

(i) SEQUENCE CHARACTERISTICS:
```

(A) LENGTH: 28 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:39:

Ala Ile Thr Phe Gly Gly Leu Leu Gly Glu Lys Thr Arg Asn Gln Met
1               5                   10                  15

Gly Val Ser Glu Leu Leu Ile Ser Thr Ala Val Gln
            20                  25

(2) INFORMATION FOR SEQ ID NO:40:

(i) SEQUENCE CHARACTERISTICS:
            (A) LENGTH: 28 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:40:

Val Phe Glu Glu Ala Phe Phe Ser Phe Cys Glu Thr Asn Gly Leu Glu
1               5                   10                  15

Tyr Ile Val Gly Arg Val Trp Ile Gly Phe Trp Leu
            20                  25

(2) INFORMATION FOR SEQ ID NO:41:

(i) SEQUENCE CHARACTERISTICS:
            (A) LENGTH: 58 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:41:

Thr Gln Glu Ile Phe Ser Phe Leu Ile Ser Leu Ile Phe Ile Tyr Glu
1               5                   10                  15

Thr Phe Ser Lys Leu Ile Lys Ile Phe Gln Asp His Pro Leu Gln Lys
            20                  25                  30

Thr Tyr Asn Tyr Asn Val Leu Met Val Pro Lys Pro Gln Gly Pro Leu
        35                  40                  45

Pro Asn Thr Ala Leu Leu Ser Leu Val Leu
    50                  55

(2) INFORMATION FOR SEQ ID NO:42:

(i) SEQUENCE CHARACTERISTICS:
            (A) LENGTH: 48 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:42:

Val Asp Phe Phe Ile Gln Asp Thr Tyr Thr Gln Lys Leu Ser Val Pro
1               5                   10                  15

Asp Gly Phe Lys Val Ser Asn Ser Ser Ala Arg Gly Trp Val Ile His
            20                  25                  30

Pro Leu Gly Leu Arg Ser Glu Phe Pro Ile Trp Met Met Phe Ala Ser

```
                 35                  40                  45
```

(2) INFORMATION FOR SEQ ID NO:43:

(i) SEQUENCE CHARACTERISTICS:
        (A) LENGTH: 58 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Leu Ser Gly Ile Gln Leu Phe Asp Arg Ile Leu Leu Leu Phe Lys Pro
1               5                  10                  15

Pro Lys Tyr His Pro Asp Val Pro Tyr Val Lys Arg Val Lys Thr Trp
                 20                  25                  30

Arg Met His Leu Phe Thr Gly Ile Gln Ile Ile Cys Leu Ala Val Leu
                 35                  40                  45

Trp Val Val Lys Ser Thr Pro Ala Ser Leu
                 50                  55
```

(2) INFORMATION FOR SEQ ID NO:44:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

```
Phe Ser Phe Cys Glu Thr Asn Gly Leu Glu Tyr Ile
1               5                  10
```

(2) INFORMATION FOR SEQ ID NO:45:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = Tyr, Phe or Ala"

(ix) FEATURE:
        (A) NAME/KEY: Modified-site
        (B) LOCATION: 2
        (D) OTHER INFORMATION: /product= "OTHER"
            /note= "Xaa = unobstructive amino acid
            residue, preferably Ala, Val, Leu, Ile,
            Met, Gly, Ser, Thr, Gln or Asn"

(ix) FEATURE:
        (A) NAME/KEY: Modified-site
        (B) LOCATION: 4..6
        (D) OTHER INFORMATION: /product= "OTHER"
            /note= "Xaa = unobstructive amino acid
            residue, preferably Ala, Val, Leu, Ile,
            Met, Gly, Ser, Thr, Gln or Asn"

(ix) FEATURE:
        (A) NAME/KEY: Modified-site
        (B) LOCATION: 7

(D) OTHER INFORMATION: /product= "OTHER"
                    /note= "Xaa = positively charged amino
                    acid residue (e.g., Lys or His)"

(xi) SEQUENCE DESCRIPTION: SEQ ID NO:45:

Xaa Xaa Lys Xaa Xaa Xaa Xaa
1               5

(2) INFORMATION FOR SEQ ID NO:46:

(i) SEQUENCE CHARACTERISTICS:
                (A) LENGTH: 10 amino acids
                (B) TYPE: amino acid
                (C) STRANDEDNESS:
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product= "OTHER"
                    /note= "Xaa = hydrophobic amino acid
                    residue (e.g., Phe, Ala, Val, Leu or
                    Ile"

(ix) FEATURE:
                (A) NAME/KEY: Modified-site
                (B) LOCATION: 2
                (D) OTHER INFORMATION: /product= "OTHER"
                    /note= "Xaa = either hydrophobic amino
                    acid residue (e.g., Phe, Ala, Val, Leu
                    or Ile) or unobstructive amino acid
                    residue, preferably Ala, Val, Leu, Ile,
                    Met, Gly, Ser, Thr, Gln or Asn"

(ix) FEATURE:
                (A) NAME/KEY: Modified-site
                (B) LOCATION: 3
                (D) OTHER INFORMATION: /product= "OTHER"
                    /note= "Xaa = hydrophobic amino acid
                    residue (e.g., Phe, Ala, Val, Leu or
                    Ile"

(ix) FEATURE:
                (A) NAME/KEY: Modified-site
                (B) LOCATION: 4
                (D) OTHER INFORMATION: /product= "OTHER"
                    /note= "Xaa = unobstructive amino acid
                    residue, preferably Ala, Val, Leu, Ile,
                    Met, Gly, Ser, Thr, Gln or Asn"

(ix) FEATURE:
                (A) NAME/KEY: Modified-site
                (B) LOCATION: 5
                (D) OTHER INFORMATION: /product= "OTHER"
                    /note= "Xaa = negatively charged amino
                    acid residue (e.g., Glu or Asp)"

(ix) FEATURE:
                (A) NAME/KEY: Modified-site
                (B) LOCATION: 6..9
                (D) OTHER INFORMATION: /product= "OTHER"
                    /note= "Xaa = unobstructive amino acid
                    residue, preferably Ala, Val, Leu, Ile,
                    Met, Gly, Ser, Thr, Gln or Asn"

(ix) FEATURE:
                (A) NAME/KEY: Modified-site
                (B) LOCATION: 10
                (D) OTHER INFORMATION: /product= "OTHER"
                    /note= "Xaa = negatively charged amino
                    acid residue (e.g., Glu or Asp)"

(xi) SEQUENCE DESCRIPTION: SEQ ID NO:46:

Xaa Xaa Xaa Xaa Xaa Xaa Xaa Xaa Xaa Xaa

-continued

```
1               5                   10
```

(2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = hydrophobic amino acid
            residue (e.g., Phe, Ala, Val, Leu or
            Ile"

(ix) FEATURE:
        (A) NAME/KEY: Modified-site
        (B) LOCATION: 2
        (D) OTHER INFORMATION: /product= "OTHER"
            /note= "Xaa = unobstructive amino acid
            residue, preferably Ala, Val, Leu, Ile,
            Met, Gly, Ser, Thr, Gln or Asn"

(ix) FEATURE:
        (A) NAME/KEY: Modified-site
        (B) LOCATION: 3
        (D) OTHER INFORMATION: /product= "OTHER"
            /note= "Xaa = hydrophobic amino acid
            residue (e.g., Phe, Ala, Val, Leu or
            Ile"

(ix) FEATURE:
        (A) NAME/KEY: Modified-site
        (B) LOCATION: 4
        (D) OTHER INFORMATION: /product= "OTHER"
            /note= "Xaa = unobstructive amino acid
            residue, preferably Ala, Val, Leu, Ile,
            Met, Gly, Ser, Thr, Gln or Asn"

(ix) FEATURE:
        (A) NAME/KEY: Modified-site
        (B) LOCATION: 5
        (D) OTHER INFORMATION: /product= "OTHER"
            /note= "Xaa = negatively charged amino
            acid residue (e.g., Glu or Asp)"

(ix) FEATURE:
        (A) NAME/KEY: Modified-site
        (B) LOCATION: 6..9
        (D) OTHER INFORMATION: /product= "OTHER"
            /note= "Xaa = unobstructive amino acid
            residue, preferably Ala, Val, Leu, Ile,
            Met, Gly, Ser, Thr, Gln or Asn"

(ix) FEATURE:
        (A) NAME/KEY: Modified-site
        (B) LOCATION: 10
        (D) OTHER INFORMATION: /product= "OTHER"
            /note= "Xaa = negatively charged amino
            acid residue (e.g., Glu or Asp)"

(xi) SEQUENCE DESCRIPTION: SEQ ID NO:47:

```
Xaa Xaa Xaa Xaa Xaa Xaa Xaa Xaa Xaa Xaa
1               5                   10
```

(2) INFORMATION FOR SEQ ID NO:48:

(i) SEQUENCE CHARACTERISTICS:
        (A) LENGTH: 10 amino acids
        (B) TYPE: amino acid
        (C) STRANDEDNESS:

```
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = hydrophobic amino acid
                residue (e.g., Phe, Ala, Val, Leu or
                Ile"

(ix) FEATURE:
            (A) NAME/KEY: Modified-site
            (B) LOCATION: 2
            (D) OTHER INFORMATION: /product= "OTHER"
                /note= "Xaa = negatively charged amino
                acid residue (e.g., Glu or Asp)"

(ix) FEATURE:
            (A) NAME/KEY: Modified-site
            (B) LOCATION: 3..7
            (D) OTHER INFORMATION: /product= "OTHER"
                /note= "Xaa = unobstructive amino acid
                residue, preferably Ala, Val, Leu, Ile,
                Met, Gly, Ser, Thr, Gln or Asn"

(ix) FEATURE:
            (A) NAME/KEY: Modified-site
            (B) LOCATION: 8
            (D) OTHER INFORMATION: /product= "OTHER"
                /note= "Xaa = negatively charged amino
                acid residue (e.g., Glu or Asp)"

(ix) FEATURE:
            (A) NAME/KEY: Modified-site
            (B) LOCATION: 9
            (D) OTHER INFORMATION: /product= "OTHER"
                /note= "Xaa = unobstructive amino acid
                residue, preferably Ala, Val, Leu, Ile,
                Met, Gly, Ser, Thr, Gln or Asn"

(ix) FEATURE:
            (A) NAME/KEY: Modified-site
            (B) LOCATION: 10
            (D) OTHER INFORMATION: /product= "OTHER"
                /note= "Xaa = hydrophobic amino acid
                residue (e.g., Phe, Ala, Val, Leu or
                Ile"

(xi) SEQUENCE DESCRIPTION: SEQ ID NO:48:

Xaa Xaa Xaa Xaa Xaa Xaa Xaa Xaa Xaa Xaa
1               5                   10

(2) INFORMATION FOR SEQ ID NO:49:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:49:

Phe Xaa Phe Xaa Glu Xaa Xaa Xaa Xaa Glu
1               5                   10

(2) INFORMATION FOR SEQ ID NO:50:

(i) SEQUENCE CHARACTERISTICS:
            (A) LENGTH: 10 amino acids
            (B) TYPE: amino acid
            (C) STRANDEDNESS:
            (D) TOPOLOGY: linear
```

-continued

```
    (ii) MOLECULE TYPE: peptide (xi) SEQUENCE DESCRIPTION: SEQ ID NO:50:

Phe Glu Xaa Xaa Xaa Xaa Xaa Glu Xaa Phe
1               5                   10
```

COMPOSITIONS AND METHODS FOR REDUCING ADHESIVENESS OF DEFECTIVE RED BLOOD CELLS

BACKGROUND OF THE INVENTION

The present invention relates to compositions and methods for use in reducing the adhesiveness of pathologically adhesive red blood cells (as hereinafter defined). In particular, the present invention is directed to compositions and methods for treatment of various conditions involving red blood cells with pathologically increased adhesiveness, for example as a result of malaria, sickle cell disease, thalassemia or diabetes.

This invention was made with Government support under Grant No. R01 AJ32995 and R01 DK16095, awarded by the National Institutes of Health. The Government has certain rights in this invention.

Sickle cell disease is a result of the presence of the altered gene product hemoglobin S. This disease is characterized by hemolytic anemia and complications resulting from episodic vaso-occlusive events, and despite the fact that more than 50 years have elapsed since the existence of a "vicious cycle" of sickling and erythrostasis was reported [Ham and Castle (1940) *Trans. Assoc. Am. Physicians* 55, 127–132], there still remain significant gaps in understanding of the mechanisms whereby sickle hemoglobin leads to the various manifestations of this disorder. Although the tendency of hemoglobin S to polymerize with reduced oxygen tension is the fundamental abnormality in sickle cell disease, polymerization and sickling itself do not entirely explain the pathophysiology of this disorder. In particular, membrane alterations in the sickle red cell contribute to sickle cell disease. The well-recognized complications of this syndrome such as recurrent and episodic painful crises, ischemic damage to tissues and organs, increased infections, and stroke presumably result from local disturbances in blood flow. The debilitating episodes of sickle cell crisis have been difficult to manage other than with hydration and analgesia.

Investigations have centered on the interaction of the sickle red cell and the vascular endothelial cell, in an attempt to identify those factors that could provoke a delay in microvascular flow. It was found that sickle red cells had a higher degree of adhesiveness to cultured human vascular endothelial cells than normal cells, and that this required neither frank morphologic deformation of the cells nor deoxygenation [Hoover et al. (1979) *Blood* 54, 872–876; Hebbel, R. P. et al. (1980) *J. Clin. Invest.* 65, 154–160]. This seminal observation with human umbilical vein endothelial cells was later confirmed both in static and flow systems using endothelial cells from a variety of tissues, and from mammalian sources other than humans. Significantly, among patients with sickle cell anemia, frequency of acute vaso-occlusive crises correlates with red blood cell adherence to endothelium. Accordingly, sickle cell adherence to endothelium was identified as the likely factor that initiates acute vaso-occlusion in sickle-cell disease, either by primarily occluding small vessels or by slowing microvascular blood flow so that secondary, reversible red blood cell sickling can occur.

Alterations in the surface of the sickle red cell involve changes in the distribution of surface charge, evidenced by the clustering of cationized ferritin on the surface of such cells; this was not found on cells containing normal hemoglobin [Hebbel & Eaton (1982) in *Membranes and Genetic Disorders*, A.R. Liss Inc., NY, pp. 311–349]. Calcium loading of normal cells induced both endothelial adherence and surface clumping of cationized ferritin. The binding of sickle cells might thus involve a redistribution of proteins. The mechanisms that might underlie such redistribution, however, were not revealed.

In the normal red cell, the integral proteins glycophorin and band 3 are randomly distributed in the membrane. Treatments of red cells to produce hemoglobin denaturation (hemichrome formation), ATP depletion, calcium loading, and oxidative cross-linking can all result in the formation of clusters of integral membrane proteins which may be visualized by freeze fracture electron microscopy. Clusters of intramembranous particles (composed principally of band 3 and glycophorin) are apparent at sites of brilliant cresyl blue induced hemichrome binding in α-thalassemic cells [Lessin, L. S. et al. (1972) *Arch. Intern. Med.* 129:306–319], in phenylhydrazine-treated cells [Low, P. S. (1989) in *Hematology, Red Blood Cell Membranes: Structure, Function, Clinical Implications*, Vol. 11, P. Agre & J. C. Parker, eds., Marcel Dekker, Inc., pp. 237–260], in erythrocytes that contain mature forms of *P. falciparum* [Allred, D. R. et al. (1986) *J. Cell Science* 81:1–16], and in irreversibly sickled cells [Lessin, L. S. et al. (1974) *Proceedings of 1st Natl. Sympos. on Sickle Cell Disease*, NIH, Bethesda, Md., pp. 213–214]. The processes that might drive such intramembrane clustering reactions in vivo have heretofore not been elucidated.

Sickle red cells generate excessive amounts of superoxide due to accelerated auto-oxidation of sickle heme [Hebbel et al. (1982) *J. Clin. Inv.* 70, 1253–1259]. This oxidant damage affects cellular hydration, increases hemichrome levels, causes the formation of hemichrome-stabilized membrane protein aggregates within the cell, and enhances adhesiveness. These same phenomena can be simulated in normal red cells by calcium loading or by treatment with the oxidant phenazine methosulfate [Hebbel et al. (1989) *Am. J. Physiol.* 256, C579–C583]. Further, free iron is non-randomly associated with the co-clusters of hemichrome and band 3 [Repka et al. (1993) *Blood* 82, 3204–3210], and could provide additional oxidant stress, focus damage to the underlying membrane structure, and promote further local hemichrome formation.

Adhesiveness is also observed in malaria-infected red cells. The hallmark of *P. falciparum* infections is sequestration, that is, attachment of erythrocytes infected with the mature stages of the parasite to the endothelial cells lining the post-capillary venules. This occurs principally in the lung, kidney, liver, heart and brain [Aikawa, M. et al. (1990) *Am. J. Trop. Med. Hygiene* 43:30–37; Pongponratn, E. et al. (1991) *Am. J. Trop. Med. Hygiene* 44:168–175]. Sequestration may totally occlude blood flow and result in tissue ischemia, coma, and death.

As with sickle and *P. falciparum*-infected erythrocytes the red blood cells from patients with diabetes have an abnormal adherence to the endothelium [Chappet, O. et al. (1994) *Nouv. Rev. Fr. Hematol.* 36: 281–288]. The mortality and morbidity from diabetes are related to the vascular complications resulting from vasoocclusion as well as capillary damage, and more than 75% of diabetic patients die from vascular complications. One of the consequences of the high concentrations of glucose in the blood plasma is the non-enzymatic glycosylation (glycation) of a variety of proteins such as those of the red cell membrane as well as hemoglobin. The early glycation products undergo a slow series of chemical rearrangements to form irreversible advanced glycation end products (AGE) and these accumulate over the lifetime of the proteins, including those of the erythrocyte.

The AGEs are potentially pathogenic, and bind to receptors on the endothelium. Band 3 protein is easily accessible to glycation, and abnormal clustering of intramembranous particles has been shown for diabetic red cells [Rambini, R. et al. (1993) *Membrane Biochemistry* 10: 71–80]. Therefore, it is likely that alterations in the conformation of band 3, in concert with fibrinogen and to a lesser extent fibronectin, play a role in the enhanced adhesion of the red cell in diabetics.

The presence of sickle hemoglobin, hemoglobin S, is the underlying cause of sickle cell disease. The thalassemias are disorders of the red cell which involve a decreased synthesis of either of the protein chains of adult hemoglobin, hemoglobin A. This lack of coordination in synthesis leads to an accumulation of one chain relative to the other, and as a consequence the free chains aggregate and accumulate as insoluble inclusions at the inner face of the membrane, bound principally to band 3 protein. Erythrocytes from patients with thalassemia bind to endothelial cells to a greater degree than do normal red cells, and such patients have greater risk of vascular occlusion. Addition of autologous platelet-rich plasma causes a further increase in the number of adherent thalassemic red cells [Butthep, P. et al. (1992) *S.E. Asian J. Trop. Med. and Public Hlth.* 23, suppl 2, 101–104]. Thalassemic cells are enriched in calcium, the membranes of such cells when extracted with the non-ionic detergent Triton X-100 retain twice the amount of band 3 as does that of the normal red cell, and clusters of intramembranous particles (composed primarily of band 3 and glycophorin) are apparent at sites of brilliant cresyl blue induced hemichrome binding in thalassemic cells [Lessin, L. et al. (1972) *Arch. Int. Med.* 129:306–319]. Despite the fact that thalassemia and sickle cell disease are due to different genes, in both syndromes the red cell is similarly altered.

It is an object of the present invention to provide compositions and methods which are useful in reducing the adhesiveness of red blood cells which exhibit enhanced adhesive properties relative to normal red blood cells (e.g., sickle cells, malaria-infected red cells, thalassemic red cells, and red cells from diabetics).

SUMMARY OF THE INVENTION

In accordance with the present invention, peptide sequences and analogs thereof based on amino acid motifs in band 3 are provided which are effective in reducing the adhesiveness of pathologically adhesive red blood cells (as hereinafter defined). In accordance with a first aspect of the invention, the sequences are characterized by the sequence motif $Z^1xKxxx+$ (SEQ ID NO:45), wherein $Z^1$ is selected from the group consisting of tyrosine, phenylalanine and alanine; x is an unobstructive residue (as hereinafter defined) and + is a positively charged residue (e.g., K or H). Methods for reducing adhesiveness in the treatment of sickle cell disease, thalassemia and diabetes are contemplated as part of this first aspect of the invention. In accordance with a second aspect of the invention, the sequences are characterized by the sequence motif $Z^2Z^3Z^2x$-xxxx- (SEQ ID NO:46), wherein $Z^2$ represents a hydrophobic residue, x is an unobstructive residue, $Z^3$ is either $Z^2$ or x and − is a negatively charged residue. Methods for treatment of malaria as well as for reducing adhesiveness in the treatment of sickle cell disease, thalassemia and diabetes are contemplated as part of this second aspect of the invention.

BRIEF DESCRIPTION OF THE DRAWINGS

The invention may be better understood with reference to the accompanying drawings, in which.

DETAILED DESCRIPTION OF THE INVENTION

Pursuant to the present invention, the central role of modifications in the anion transporter band 3 protein in the enhanced adhesiveness of certain red blood cells was explored. Band 3 protein is present in a million copies per red cell in the form of monomers, dimers, or tetramers. Its molecular weight is approximately 95,000 kDa. There are two distinct domains: a 43 kDa water-soluble cytoplasmic domain, and a 55 kDa membrane-spanning domain [Low, P. S. (1986) *Biochimica et Biophysica Acta* 864, 145–167].

Figure 1:
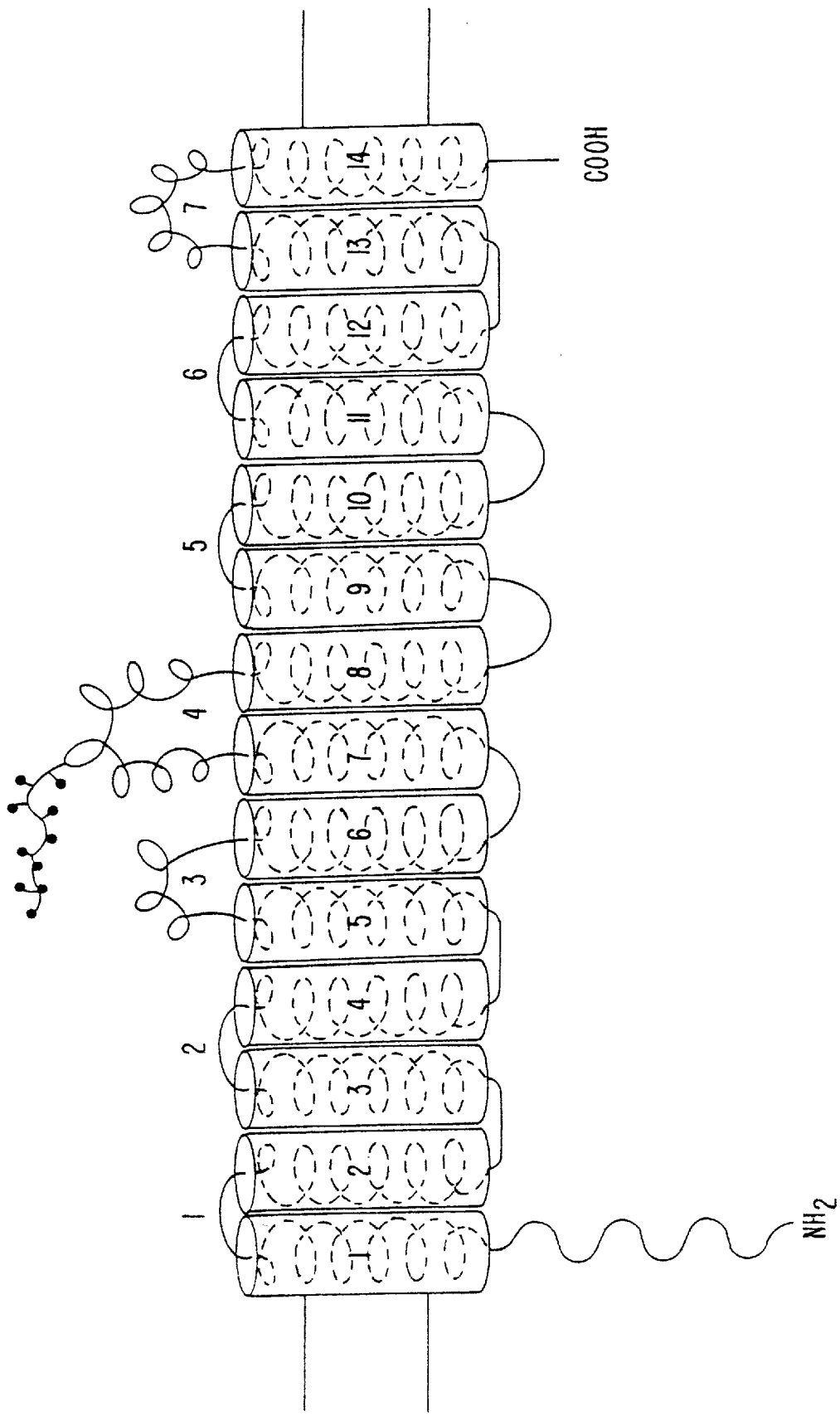
FIG. 1 illustrates the secondary structure of band 3 protein.

The gene for band 3 protein has been cloned and sequenced [Tanner, M. J. et al (1988) *Biochem. J.* 256, 703–12; Lux, S. E. et al. (1989) *Proc. Nat'l Acad. Sci. USA* 86, 9089–93]. From these published sequences (to which reference is made herein with respect to residue numbers relating sequences of interest herein to locations in the band 3 protein gene) and information about the hydrophobicity and hydrophilicity of amino acids in the sequence and observed features of the protein (e.g., flexibility of protein segments, reactivity of residues in intact cell), it was possible to derive a working 2-dimensional profile of band 3. FIG. 1 illustrates a prediction of which regions of the band 3 molecule are exofacial and which are membrane spanning. Division of sequences into external loop regions was based on hydropathy plots and published amino acid sequence information [Tanner et al. (1988), sapra; Lux et al. (1989), supra].

The present invention is based in part upon the recognition that modifications in band 3 occur in a number of otherwise-unrelated conditions (e.g., malaria, sickle cell disease, thalassemia, diabetes) such that there is clustering and a change in the conformation of this protein. As a consequence of this rearrangement, once cryptic adhesive sites become exposed. By this change in protein conformation and exposure, the normally non-adherent erythrocyte becomes a cell with enhanced endothelial adhesiveness.

Several of the peptides employed in accordance with the present invention were first identified in the course of examination of the properties of malaria-infected erythrocytes. A number of in vitro red cell adhesion models for malarial sequestration using human umbilical vein endothelial cells and amelanotic melanoma cells have been described [Udeinya, I. et al. (1981) *Science* 213:555–557; Schmidt et al. (1982) *J. Clin. Inv.* 70, 379–386]. These in vitro systems were used to search for the molecule on the surface of the *P. falciparum*-infected red cell that mediated adhesion.

In a search for this putative adhesin, murine monoclonal antibodies (Mabs) against live *P. falciparum*-infected red cells were prepared [Winograd, E. and Sherman, I. (1989) *J. Cell Biol*, 108, 23–30; Crandall, I. and Sherman, I. (1991) *Parasitology* 102, 335–340]. These Mabs recognized only red cells bearing mature stages of *P. falciparum*, and did not react with uninfected, aged, or ring-infected red cells. Several of these Mabs blocked cytoadherence in a dose-dependent manner.

Since none of these Mabs reacted with the intracellular parasite or immunoprecipitated parasite-encoded proteins, it appeared that the antigen was related to a membrane protein of the red cell. By peptide mapping of the antigens immunoprecipitated by these Mabs from surface iodinated red cells, it was possible to show that the infected red cell antigens were homologous to band 3 protein.

Using the anti-falciparum and anti-band 3 Mabs with unsealed and sealed red cells, it was possible to localize the epitopes of band 3 recognized by the adherence-blocking Mabs. The epitopes were confined to putative exofacial loops 3 and 7 of band 3, but not loop 4 (which contains the sugar).

Several synthetic peptides corresponding to these epitopes were tested for their capacity to inhibit the adherence of *P. falciparum*-infected red cells. The most active peptides with $IC_{50}$s in the micromolar range contained the sequences: HPLQKTY [SEQ ID NO:1] and YVKRVK [SEQ ID NO:2] [Crandall, I. et al. (1993) *Proc. Natl. Acad. Sci. USA* 90, 4703–4707]. These peptides were named pfalhesin (for *P. falciparum* adhesin).

Murine monoclonal and primate and rabbit polyclonal sera prepared against synthetic pfalhesin reacted only with the surface of infected red cells bearing mature stage parasites (and not uninfected or ring-infected red cells). In addition, the antibodies blocked the adherence of these cells in a dose dependent manner [Crandall and Sherman (1994) *Parasitology* 108, 389–396]. These findings indicated that exposure of cryptic residues of band 3 were responsible for the adhesiveness of the *P. falciparum* infected red cell. A murine monoclonal antibody (Mab) generated against synthetic peptides composed only of amino acids 542–555 of human band 3 recognized only infected red cells and blocked their adherence, whereas another Mab prepared against intact band 3 and which recognized this same amino acid sequence recognized all red cells and did not block the adherence of infected cells. These results demonstrated that Mabs reactive with a common amino acid sequence may bind to different conformations of that sequence, and suggested that the adherence of *P. falciparum*-infected red cells may result from a change in the surface topography of the band 3 protein.

Knowledge of the red cell adhesin in *P. falciparum*-infected red cells and its peptide analog also permitted identification of the receptor on the target cell. Using Chinese hamster ovary (CHO) cells transfected with genes encoding for either ICAM-1 or CD36, it was shown that pfalhesin and CD36 formed an adhesin/receptor pair. CD36-mediated adherence was non-competitively inhibited by monoclonal antibodies both to synthetic peptides patterned on band 3 and to live *P. falciparum*-infected red cells, and was competitively inhibited by pfalhesin. Immobilized pfalhesin used as an affinity matrix purified only CD36 from cell extracts [Crandall et al. (1994) *Experimental Parasitology* 75, 203–209].

Pfalhesin was active both in vitro and in vivo in Saimiri and Aotus monkeys, whereas peptide with a scrambled array of amino acids was without effect. Strikingly, in the in vivo studies, when infected monkeys were treated with micromolar intravenous pfalhesin, a tide of infected red cells was released from sequestration sites into the peripheral circulation [Crandall et al. (1993), supra]. Both the L- and D-forms of the pfalhesin peptides effectively inhibited adhesion.

In accordance with an aspect of the present invention, it has been determined that the enhanced adhesiveness of sickle cells appears to involve modifications in band 3 protein similar to those observed in *P. falciparum*-infected red cells. Therefore, synthetic peptides based on cryptic amino acid sequences of band 3 block sickle cell binding. The adhesion of sickle red cells to the vascular endothelium is likely critical to the initiation or amplification of the episodic vasoocclusive events of sickle cell disease. Increased adhesion in the microcirculation promotes stasis, sickling, and platelet entrapment and activation. The early pathologic lesions found in the lungs of a mildly hypoxic SAD mouse model of sickle cell disease show early unorganized thrombi composed of sickle cells, platelet aggregates, and fibrin deposits precisely consistent with this scenario. In addition, in a study using the ex vivo mesocecum vasculature of the rat [Kaul, D. K. et al. (1989) *Proc. Natl. Acad. Sci. USA* 86, 3356–3360], a single bolus of washed oxy-normal erythrocytes or oxy-sickle cells (unseparated or density-defined sickle cell classes) was infused, and by hemodynamic monitoring and intravital microscopic observations of the microvascular flow, higher peripheral resistance for sickle erythrocytes and adherence of these cells exclusively to the venular endothelium, but rare or no adherence of oxy-normal cells, were revealed. Both of these models can be used to test the in vivo efficacy of synthetic peptides in remediating the microvascular adhesion of red cells characteristic of sickle cell anemia. The therapeutic benefits of intravenous infusion of synthetic peptides (usually at doses of ~500 μg in rodents) have been demonstrated in a number of contexts, such as the following: in a mouse model wherein metastasis of liver and lung tumors was reduced [Saiki, I. et al. (1993) *Japanese J. Cancer Research* 84:326–335; Saiki, I. et al. (1993) *Japanese J. Cancer Research* 84:558–565; Komuzawa, H. et al. (1993) *Biological & Pharmaceutical Bull.* 16:997–1003]; in reducing the recruitment of leukocytes into the subarachnoid space in a meningitis model [Sandros, J. et al. (1994) *Microbial Pathogenesis* 16:213–220]; in blocking neovascularization in the rat cornea [Tolsma, S. S. et al. (1993) *J. Cell Biol.* 122:497–511]; and in inhibiting platelet adhesion in vivo [Ito, S. et al. (1992) *Intl. J. Artificial Organs* 15:737–45]. It is therefore anticipated that anti-adhesion therapy with synthetic peptides at very low doses (i.e., milligrams to obtain micromolar plasma levels) will be effective in vivo in reversing or preventing the vasoocclusive events of sickle cell disease.

In accordance with a first particular aspect of the present invention, there are provided peptide sequences characterized by the sequence motif $Z^1$xKxxx+ (SEQ ID NO:45), wherein Z is selected from the group consisting of tyrosine, phenylalanine and alanine (preferably, tyrosine or phenylalanine); K is a lysine residue; x is an unobstructive residue; and + is a positively charged residue (in the native band 3 protein a lysine or a histidine residue). In accordance with this aspect of the present invention, it has been determined that such sequences are useful in reducing cell adhesion in sickle cell disease, thalassemia and diabetes.

Alanine substitution experiments indicated that alanine is tolerated in the $Z^1$ residue position, an observation consistent with previous observations (e.g., iodination of the peptides results in incorporation of iodine atoms into tyrosine residues which abolishes peptide-blocking activity and suggests that the Z residue participates in a hydrophobic interaction with the receptor, CD36). The advantage of the presence of the preferred $Z^1$ group tyrosine or phenylalanine can be inferred from the observations that 1) both active forms of the peptide (HPLQKTY [SEQ ID NO:1] and YVKRVK [SEQ ID NO:2]) contain a tyrosine residue in the same relative position; and 2) the peptide YVK [SEQ ID NO:3] has an $IC_{50}$ that is 1/1000 that of lysine (K) alone.

For purposes of the present invention, the term "unobstructive residue" is defined as an amino acid residue which does not interfere with the conformation of the peptide. In preferred embodiments of the invention, x is selected from the group consisting of alanine (A), valine (V), leucine (L), isoleucine (I), methionine (M), glycine (G), serine (S), threonine (T), glutamine (Q) and asparagine (N). Most preferably, the x residue in the human band 3 sequence is selected from the group consisting of valine (V), leucine (L), arginine (R), glutamine (Q), and threonine (T). Experimental evidence indicates that alanine (A) can be substituted for any x position and the peptide retains its activity. Substitution of a large (e.g., tyrosine, phenylalanine, tryptophan or histidine) or inappropriately charged (e.g., aspartic acid or glutamic acid) residue into an x position would be expected to have a negative effect on the peptide/CD36 interaction and is therefore not preferred.

The presence of x residues is necessary since the spacing between the K residue and the + residue is important to the activity of the peptide. For example, the shortened peptide HPQKTY [SEQ ID NO:4] is inactive, whereas the lengthened peptide HPLGQKTY [SEQ ID NO:5] retains its activity.

The + residue is observed to be a lysine in the sequence YVKRVK [SEQ ID NO:2] and a protonated histidine residue in the sequence HPLQKTY [SEQ ID NO:1]. Latex microspheres coated with one or the other of these sequences indicate that the sequence HPLQKTY [SEQ ID NO:1] displays pH dependency (as observed in an infected erythrocyte/CD36 interaction) while the sequence YVKRVK [SEQ ID NO:2] does not. Microsphere studies indicate that the peptide HPLQKTY [SEQ ID NO:1] has a higher affinity for CD36 than YVKRVK [[SEQ ID NO:2] and is the more active peptide competitor in vitro (as well as the only active adhesive sequence of the two in vivo).

Preliminary experiments employed the overlapping peptides identified in Table 1.

TABLE 1

| Peptide | Sequence | Comment | SEQ ID NO: |
|---|---|---|---|
| 3a | DHPLQKTYNY | residues 546–555 | 6 |
| 4 | YTQKLSVPDGFKVSN | residues 628–642 | 7 |
| 3b | KLIKIFQKHPLQKTY | residues 539–553 | 8 |
| 7a | KPPKYHPDVPYVKR | residues 814–827 | 9 |
| 7b | DVPYVKRVKTWRMH | residues 821–834 | 10 |
| 3c | NYNVLMVPKPQGPLPN | residues 554–569 | 11 |
| 7c | YVKRVK | residues 824–829 | 2 |
| 3d | GHPLQKTY | residues 547–553 | 12 |
| 7d | YVK | residues 824–826 | 3 |
| 3e | YTKQLPHG | residues 553–546 | 13 |
| 7e | KPPKYHP | residues 814–820 | 14 |
| — | FVKRVKTY | based on residues 824–829 | 15 |
| 3ds | LYPQHKT | scramble of residues 547–553 | 16 |
| 3d(D) | GHPLQKTY | synthesized with D amino acids; residues 547–553 | — |
| 3f | FQDHPLQKTYNY | residues 544–555 | 17 |
| — | APLQKTY | alanine substitution based on residues 547–553 | 18 |
| — | HALQKTY | alanine substitution based on residues 547–553 | 19 |
| — | HPAQKTY | alanine substitution based on residues 547–553 | 20 |

TABLE 1-continued

| Peptide | Sequence | Comment | SEQ ID NO: |
|---|---|---|---|
| — | HPLAKTY | alanine substitution based on residues 547–553 | 21 |
| — | HPLQATY | alanine substitution based on residues 547–553 | 22 |
| — | HPLQKAY | alanine substitution based on residues 547–553 | 23 |
| — | HPLQKTA | alanine substitution based on residues 547–553 | 24 |
| — | HPLGQKTY | length altered | 25 |
| — | HPQKTY | length altered | 4 |

The peptide backbone appears to play little part in the activity of the peptide since the order of the residues can be reversed (i.e., GHPLQKTY [SEQ ID NO:12] is as active as YTKQLPHG [SEQ ID NO:13]) and the L amino acid and D amino acid forms of the peptide GHPLQKTY [SEQ ID NO:12] have equal activity. In these sequences, a G residue is added to both peptides for synthetic considerations.

In accordance with a second particular aspect of the present invention, there are provided peptide sequences characterized by the sequence motif $Z^2Z^3Z^2$x-xxxx- (SEQ ID NO:46), wherein $Z^2$ represents a hydrophobic residue (F, A, V, L, I), x represents an unobstructive residue (as defined previously), $Z^3$ is either $Z^2$ or x, and – represents a negatively charged residue (e.g., E or D). In accordance with this aspect of the invention, methods are provided for treatment of malaria as well as other conditions involving cell adhesion.

Identification of this motif was based in part on the observation that the tyrosine in pfalhesin participated in a hydrophobic interaction which did not tolerate the presence an iodine atom, and that two negative charges should be spaced in such a way that they could interact with the lysine and histidine residues of pfalhesin. Cytoadherence assays indicated that anti-band 3 mouse monoclonal 5H12 had properties inconsistent with non-competitive inhibition of the pfalhesin/CD36 interaction. PEPSCAN analysis indicated that the epitope of the antibody was FSFCETNGLE [SEQ ID NO:26], a motif that can be abbreviated to ZxZx-xxxx- (SEQ ID NO:46) a close approximation of the motif predicted to form the receptor domain of pfalhesin. Synthetic peptides based on this sequence are active in low micromolar concentrations, but do not display simple inhibition of cytoadherence.

Attempts to produce an inactive scramble of the sequence FSFCETNGLE [SEQ ID NO:26] based on residues 476–485 of band 3 led to the testing of FETLGCNEGF [SEQ ID NO:27] and FFSATLGNEE [SEQ ID NO:28]. FFSATLGNEE [SEQ ID NO:28] was inactive, but FETLGCNEGF [SEQ ID NO:27] had a reduced activity, presumably due to the presence of the motif Z-xxxxx-xZ (SEQ ID NO:48) containing a less effective form of the ZxZx-xxxx- (SEQ ID NO:47) motif in a reverse order. Alanine substitution experiments employing the peptides ASFCETNGLE [SEQ ID NO:29], FAFCETNGLE [SEQ ID NO:30], FSACETNGLE [SEQ ID NO:31], FSFAETNGLE [SEQ ID NO:32], FSFCATNGLE [SEQ ID NO:33], FSFCEANGLE [SEQ ID NO:34], FSFCETAGLE [SEQ ID NO:35], FSFCETNALE [SEQ ID NO:36], FSFCETNGAE [SEQ ID NO:37] and FSFCETNGLA [SEQ ID NO:38] confirmed that both glutamic acid residues (E) are important to the peptide's activity. FIG. 5 illustrates the results of cytoadherence assays using the peptides SEQ ID NOS:29–38. FSFCATNGLE [SEQ ID NO:33] and FSFCETNGLA [SEQ ID NO:38] produced flat lines, an indication of a lack of biological activity of the peptides. As previously noted, the effect of the other peptides is not simple (competitive) inhibition.

Initial reports that peptides related to loops 3 and 7 of band 3 could reduce the adhesiveness of malaria-infected erythrocytes were doubted by some scientists concerned with adhesion of *P. falciparum*-infected cells, because it was not immediately obvious how a membrane protein present in a million copies per red cell could form an adhesin in only a subpopulation of cells. Further work has helped to define the alterations in the band 3 protein that take place in *P. falciparum*-infected erythrocytes that produce the adhesin. Initially, this process was thought to be a direct consequence of the maturation of the parasite and therefore limited to *P. falciparum*-infected erythrocytes. The determination that the human band 3 protein contains a potential CD36 binding domain and that peptides patterned on this domain influence both *P. falciparum*-infected erythrocyte and sickle cell adhesion was non-intuitive.

Two types of structural mechanisms, which are not necessarily independent, could lead to the creation of an adhesive surface protein from a normally non-adhesive exofacially exposed membrane protein such as band 3. First, a conformational change in the band 3 molecule could simply expose a normally cryptic adhesive sequence. Second, aggregation of band 3 could occur to modify adhesiveness independently of changes in band 3 conformation. For example, aggregation could bring together sequences which were weakly adherent by themselves, but which would be strongly recognized by a cluster of adhesin receptors on the endothelial cell. Alternatively, band 3 aggregation could join non-adhesive protein sequences which together would form an adherent region. However, both of these latter mechanisms are unlikely since antibodies directed to adhesive sequences do not recognize normal cells and since beads conjugated with the peptide corresponding to loop 3 reproduce the adherence of malaria-infected red cells to endothelial cells. Therefore, it is most likely that the actual exposure of cryptic epitopes results from a conformational change in band 3. Nevertheless, because band 3 in sickle cells has been reported to be abnormally clustered [Hebbel et al. (1980), supra; Waugh, S. et al. (1986) *J. Clin. Invest.* 78:1155–1160; Schluter, K. and D. Drenckhahn (1986) *Proc. Natl. Acad. Sci. USA* 83:6137–6141; Corbett, J. D. and D. E. Golan (1993) *J. Clin. Invest.* 91:208–217], band 3 aggregation may well still be directly involved in promoting the conformational change which exposes the cryptic epitopes.

Many factors can influence sickle cell adherence in the patient with sickle cell disease. Several plasma factors, including acute phase reactants such as fibrinogen and thrombospondin, can and do influence adhesiveness. However, increased sickle cell adhesiveness can be demonstrated even in the absence of plasma, and the results reported herein showing inhibition of increased sickle cell/endothelial cytoadherence were conducted in the absence of plasma. Further, it has been convincingly shown that there is increased spontaneous oxygen radical generation in sickle erythrocytes [Hebbel et al (1982), supra], and it has been proposed that this excess oxidative activity, which may be localized to the membrane by hemichrome precipitation there, could affect membrane proteins. Since evidence for a change in the accessibility of certain interhelical peptide regions of the membrane protein band 3 has been provided, and these regions appear to be instrumental in the increased cytoadherence of sickle cells, it is reasonable to hypothesize that sickle hemoglobin itself, or sickling, effects changes in band 3 which, in turn, mediate the increased adhesiveness observed herein. Further, as increased oxidative products are generated in the process of sickling, these may be involved as intermediaries in producing the changes in band 3 and the eventual increased cytoadherence of sickle cells.

Since the primary event in adhesion appears to involve the linking of an adhesin localized on the surface of the sickle cell to its endothelial receptor and since this adhesive event may be very early in the chain of events leading to sickle cell disease, the development of therapy to block or reverse such cell-cell interactions is expected to provide benefit to these patients. Further, such therapy early in the process leading to vasoocclusion might be more specific and less toxic than other more general approaches directed against sickle cell hemoglobin polymerization.

The red cells from diabetics, those from individuals infected with *P. falciparum* malaria, and those from patients suffering from sickle cell disease and thalassemia show a common pattern: alterations in band 3 protein, evidenced by a clustering of intramembranous particles, accumulation of calcium and hemichrome, and enhanced adhesiveness for the endothelium. In the case of sickle cells and *P. falciparum*-infected red cells there is evidence that changes in the conformation of band 3 expose cryptic regions, and this contributes to the adhesive properties of these cells; further synthetic peptides based on these cryptic regions block the adherence of these red cells to the endothelium. The available data suggests that the exposure of cryptic and adhesive regions of band 3 may also occur in thalassemic and diabetic red cells. Therefore, the administration of synthetic peptides based on band 3 motifs should also block/reverse vasoocclusion in thalassemia and diabetes.

The peptides suitable for use in accordance with the present invention may readily be prepared using, e.g., conventional solid phase and solution addition methods of synthesis, as generally understood in the art. For purposes of the present invention, the term "peptide" refers to compounds comprising about 50 amino acids or less; preferably, the peptides of the present invention comprise less than about 25 amino acids, and most preferably less than about 20 amino acids. Hybrid proteins with suitable properties combining the sequences of the present invention with another protein may also be employed in accordance with the present invention; such hybrid proteins may be suitably prepared using, e.g., recombinant DNA techniques well known to those of skill in the art. In addition to sequences comprising only the typical L-form of the amino acids, use may be made of sequences comprising one or more D-amino acids, homologs and/or other modified forms of amino acids; in some preferred embodiments, sequences comprising only D-amino acids are employed. While reference is made throughout to peptides herein, it is not strictly necessary that the compounds for use in accordance with the present invention comprise only sequences of amino acids in a form corresponding to fragments of naturally-occurring proteins. To the extent that a compound contains the requisite sequence and meets the other criteria specified herein, modifications and substitutions in peptide structure currently known to those skilled in the art or which may hereinafter be developed are contemplated as within the scope of the present invention.

For purposes of treating a mammalian patient suffering from a condition involving pathologically enhanced erythrocyte adhesiveness, the peptides of the invention are administered on a regular (e.g., daily) basis at a concentration effective to prevent cell adhesion. While an appropriate amount for use with any given patient will depend upon a number of factors and may be readily be determined empirically, in general an amount of at least about 1 mg/kg, and preferably about 3 to about 10 mg/kg, of patient body weight administered intravenously in physiologic saline or orally is generally effective to reduce cell adhesion.

The invention may be better understood with reference to the accompanying examples, which are intended for purposes of illustration only and should not be construed as in any sense limiting the scope of the present invention as defined in the claims appended hereto.

EXAMPLE 1

The adherence of sickle and normal red cells to cultured human umbilical vein endothelial cells (HUVEC) was examined using a modified assay based upon a procedure reported in the literature [Hebbel, R. P. et al. (1992) *Blood* 65, 2634]. A 2.5% suspension of red cells in Hank's Buffered Saline containing 0.5% Bovine Serum Albumin was incubated with or without peptide for 40 minutes at 37° C. in 15 mm diameter plastic wells coated with a confluent monolayer of endothelial cells. The medium was removed and the wells gently washed 3 times with the incubation buffer. Adherent red cells were then visually counted at 100× in an inverted phase microscope using a 25 mm² grid centrally placed beneath the wells. The binding of sickle cells was 2 to 3 fold higher than that of control red cells: 2.4±0.5 (n=49 separate experiments; 9 patients). No significant difference in this binding result was observed when autologous plasma was substituted for the incubation buffer. Since the presence of plasma rendered the visualization of the bound red cells difficult, the following experiments were carried out in the absence of plasma. Peptide 2f, FSFCETNGLE [SEQ ID NO:26] (residues 476–485 from band 3 extracellular loop 2) and peptide 3d, GHPLQKTY [SEQ ID NO:12] (residues 547–553 from band 3 extracellular loop 3), both in the L-isomeric form and at 25 µg/ml, inhibited abnormal sickle cell binding by 95±13% (n=10; 5 patients) and 102±12% (n=17; 7 patients), respectively. This inhibitory activity was also observed in the presence of plasma. The D-isomer of peptide 3d, 3d(D), was as effective as its L-isomer (SEQ ID NO:12) in inhibiting sickle cell binding: 100±11% (n=15; 5 patients). For the above three active peptides, inhibition was maximal at 20 µg/ml, and 50% inhibition occurred at 4 µg/ml—the same concentration required for half-maximal inhibition of the binding of *P. falciparum*-infected red cells. A control scrambled sequence of peptide 3d, 3ds (LYPQHKT) [SEQ ID NO:16] at 42 µg/ml was only weakly inhibitory: 15±21% (n=15; 7 patients) and a control sequence from another connecting loop of band 3 membrane domain, 7e (KPPKYHP) [SEQ ID NO:14] (residues 814–820), was ineffective at 42 µg/ml: 12±21% (n=11; 4 patients). The peptides 2f and 3d (and not the control peptides 3ds and 7e) were also effective in blocking the cytoadherence of normal cells previously loaded with 10 µM calcium, which has been reported to mimic sickle cell adhesiveness [Hebbel et al. (1980), supra]. Because the peptide 3d binds to endothelial cells, the inhibition of cytoadherence is presumed to arise from competitive binding. These observations imply that in sickle cells at least two segments of the membrane domain of band 3 contribute to the sickle cell's abnormal adherence. They also suggest that in sickle cells band 3 has undergone a conformational rearrangement that exposes normally inaccessible connecting loops between transmembrane helices. In direct support of this conclusion, FACS scan analysis of 3 sickle patients revealed that the monoclonal antibodies 1C4 and 4A3 (directed against a normally cryptic band 3 loop sequence exposed in *P. falciparum*-infected red cells) recognized a significant fraction of red cells from patient 3, and that 1C4 also recognized a significant fraction of cells from patient 2.

EXAMPLE 2

The following experiment describes the identification of the epitope for Mab 5H12 and an examination of the effects of the antibody and of peptide sequences corresponding to the epitope on CD 36 mediated cytoadherence and rosetting. Mab 5H12 was produced by injecting mice with live red cells infected with *P. falciparum*.

Peptides were synthesized by Coast Scientific (San Diego, Calif.) using the tboc method followed by HF release. All peptides were >97% pure as determined by HPLC and mass spectrometry.

Predicted exofacial regions of band 3 protein (Table 1) were based on published data and used as the pattern for overlapping decapeptides. All peptides were patterned on the reported human band 3 amino acid sequences [Lux et al., supra; Tanner et al., supra]. Hydrophobic regions are indicated by an underline while regions with average access values of 4 or greater are indicated in bold face. Start residues of peptides with an average reactivity greater than 1.0 are marked with a dot above the residue. Hydrophobicity and access predictions indicated in Table 2 are based on a moving average value for nine amino acids (i.e., the indicated residue, four residues upstream and four residues downstream) where a negative value for the average hydrophobicity values is considered to constitute a hydrophobic region and an average access value of 4 or greater is considered to be an accessible region [Parker, J. M. R. et al. (1986) *Biochem.* 25:5425–5432]. Regions with low hydrophilicity and access values are predicted to be transmembranous.

TABLE 2

| Putative exofacial region | Residue numbers | Sequence | SEQ ID NO. |
|---|---|---|---|
| loop 1 | 420–447 | AITFGGLLGEKTRNQMGVSELLISTAVO | 39 |
| loop 2 | 470–497 | VFEEAFFSFCETNGLEYIVGRVWIGFWL | 40 |
| loop 3 | 520–577 | TQEIFSFLISLIFIYETFSKLIKIFQDHPL QKTYNYNVLMVPKPQGPLPNTALLSLVL | 41 |
| loop 4 | 620–677 | VDFFIQDTYTQKLSVPDGFKVSNSSARGWV IHPLGLRSEFPIWMMFAS | 42 |
| loop 7 | 800–857 | LSGIQLFDRILLLFKPPKYHPDVPYVKRVK TWRMHLFTGIQIICLAVLWVVKSTPASL | 43 |

PEPSCANs of putative exofacial regions were performed with decapeptides constructed with an offset of 2 amino acids. Non-cleavable peptides with acetylated C-termini were synthesized on pins by Chiron Mimotope (Australia).

The epitope of a previously described anti-*P. falciparum*-infected red cell murine monoclonal antibody, 5H12, was determined using a 1:400 dilution of ascites fluid and a goat anti-mouse IgG-alkaline phosphatase second antibody. Plates were developed in 0.5 mg/ml nitrophenol phosphate, 150 mM Tris base, 10 mM $MgCl_2$ for 1 h before being read in an ELISA plate reader (Model 450, Biorad, Richmond Calif.) at 405 nm with a reference filter of 655 nm. Results are expressed as actual optical density value subtracted from the average absorbance of 2 wells that had the peptide bearing pins removed.

The Gambian FCR-3 strain of *P. falciparum* was cultured according to the literature method [Trager, W. & J. Jensen (1976) *Science* 193:673–675]. Cultures were synchronized at the ring stage by sorbitol lysis of mature forms [Lambros, C. & J. P. Vanderberg (1980) *J. Parasitology* 65:418–20]. Knobless parasite cultures were produced from a knobby FCR-3 line and maintained as described previously [Crandall, I. E. et al. (1994) *Cell Adhesion & Communication* 2(6):503–510].

Cytoadherence assays were carried out as described previously [Udeinya et al. (1981), supra; Crandall et al. (1991), supra] except that BTS buffer (50 mM Bis Tris, 130 mM NaCl, pH 6.6) was substituted for BTC buffer (i.e. the $Ca^+$ was omitted from the cytoadherence assay buffer). Rosetting was measured as described previously [Crandall et al. (1994), supra].

Figure 2:
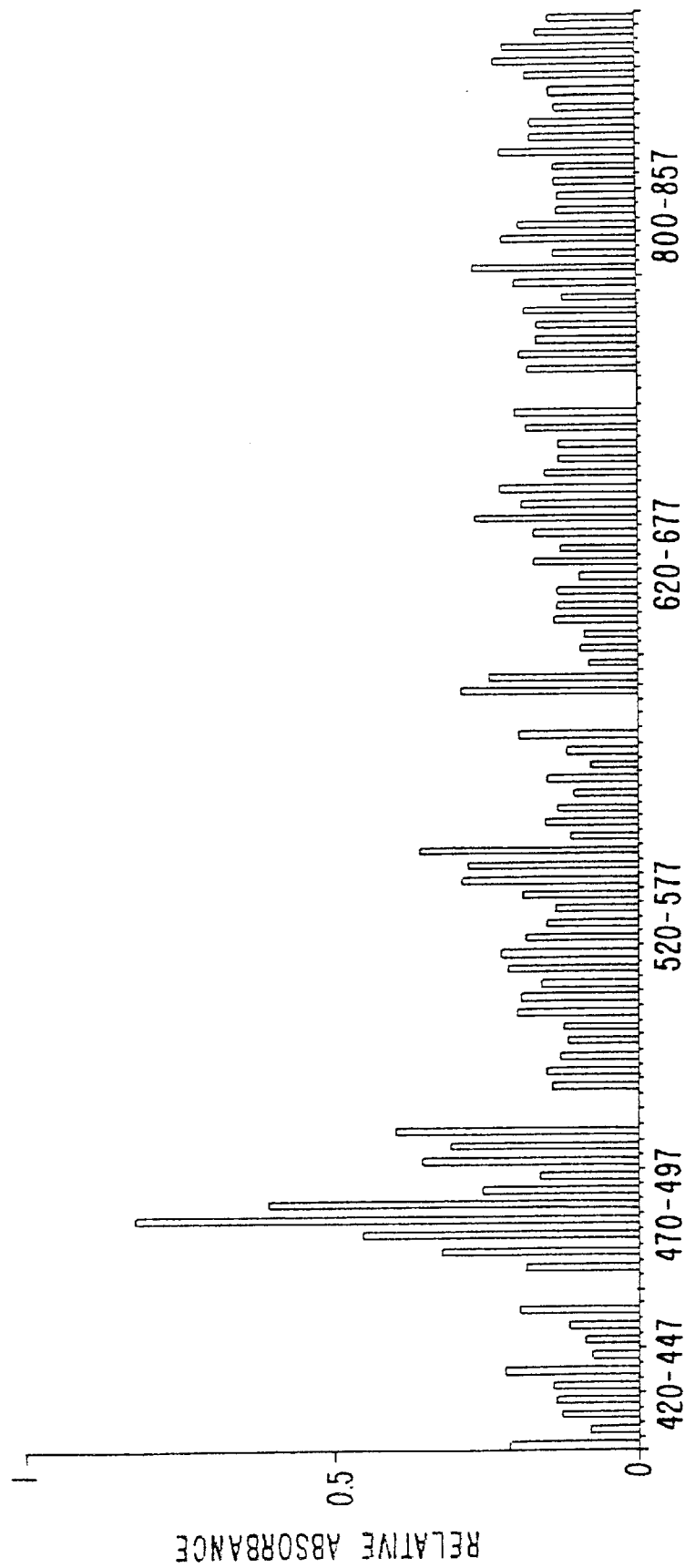
FIG. 2 illustrates PEPSCAN analysis showing that the Mab 5H12 recognizes the human band 3 protein.

PEPSCAN analysis (FIG. 2) indicates that the Mab 5H12 recognizes the human band 3 protein as previously reported. Decapeptides based on the human band 3 sequence were probed with a 1:400 dilution of ascites fluid obtained from the cell line 5H12. Absorbance at 405 nm is indicated on the y axis and the amino acid residue numbers on which the peptides are based (Table 2) are shown on the x axis. The location of the Mab's epitope is not in the region 821–834, but rather at amino acids 474–487. CD36 mediated adhesion of *P. falciparum*-infected red cells has previously been reported to be due to an interaction between normally cryptic amino acids 547–553 and CD36. Therefore, it appears that the epitope of the Mab 5H12 is on the same protein, but does not overlap the CD36 adhesin (named pfalhesin).

Attempts were made to determine if exposure of *P. falciparum*-infected red cells to the Mab 5H12 resulted in increased amounts of adhesin on the surface of the infected cell. Increasing amounts of murine 5H12 were added and the amount of residues 547–553 was determined by staining with a rabbit polyclonal directed against these residues. These experiments indicated that the amount of adhesin expressed on the surface of the *P. falciparum*-infected erythrocyte remained constant.

Pfalhesin (the adhesive conformation of human band 3 amino acids 547–553) can participate in two adhesive events, rosetting or cytoadherence. In order to determine if the Mab 5H12 was hindering one adhesive event and thereby promoting the other (i.e. 5H12 was inhibiting infected cell/uninfected cell interactions and thereby facilitating infected cell/endothelial cell interactions) the effect of the Mab on rosetting was determined. It was found that addition of increasing amounts of 5H12 inhibited the formation of rosettes in K° culture samples in a dose dependent manner.

Figure 3A:
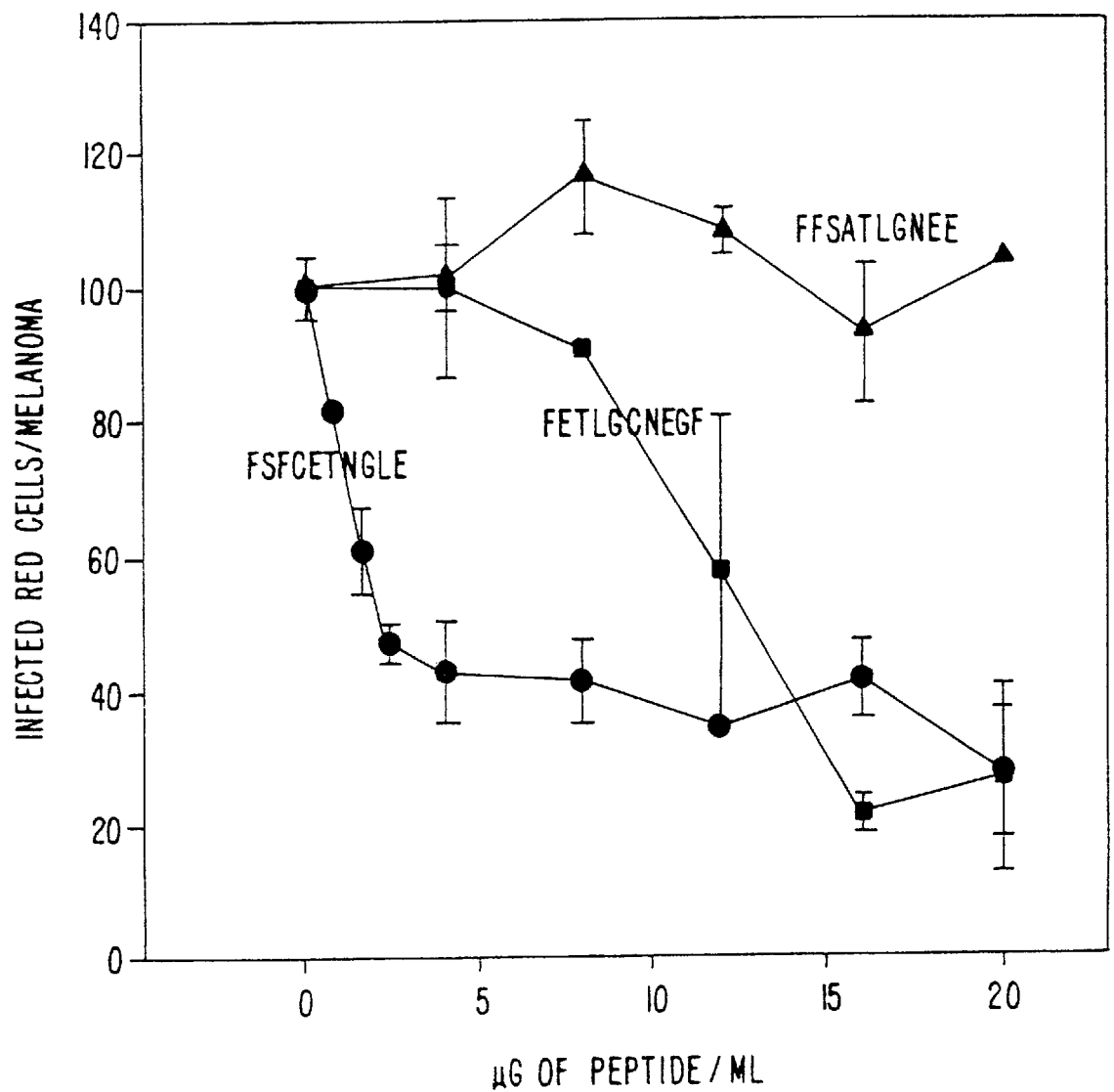
FIGS. 3A–3B illustrate the results of tests of competitive inhibition of cytoadherence (FIG. 3A) and rosetting (FIG. 3B) of *P. falciparum*-infected erythrocytes using peptides (FSFCETNGLE=SEQ ID NO:26; FETLGCNEGF=SEQ ID NO:27; FFSATLGNEE=SEQ ID NO:28) in accordance with the present invention.
Figure 3B:
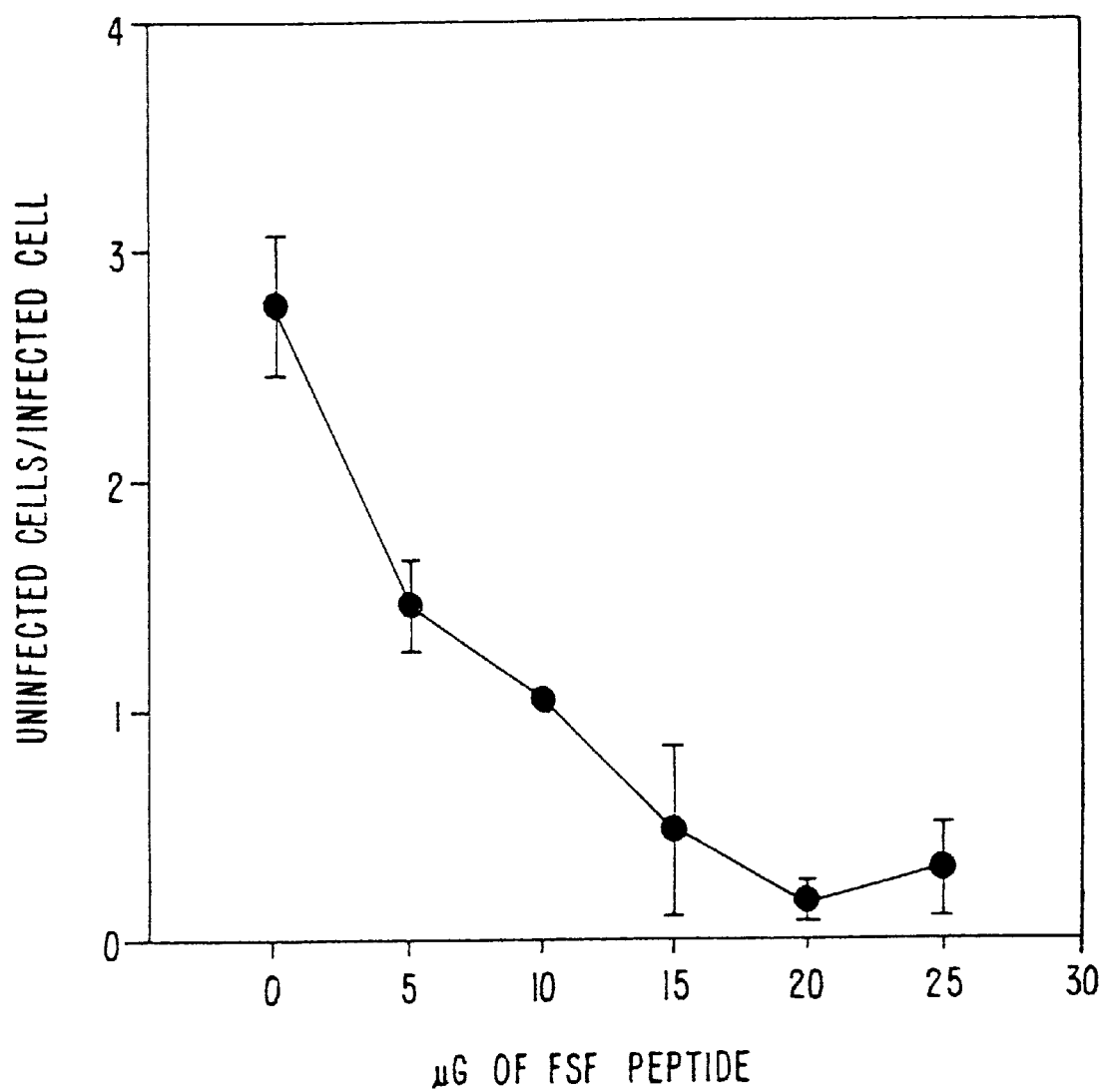
Figure 4:
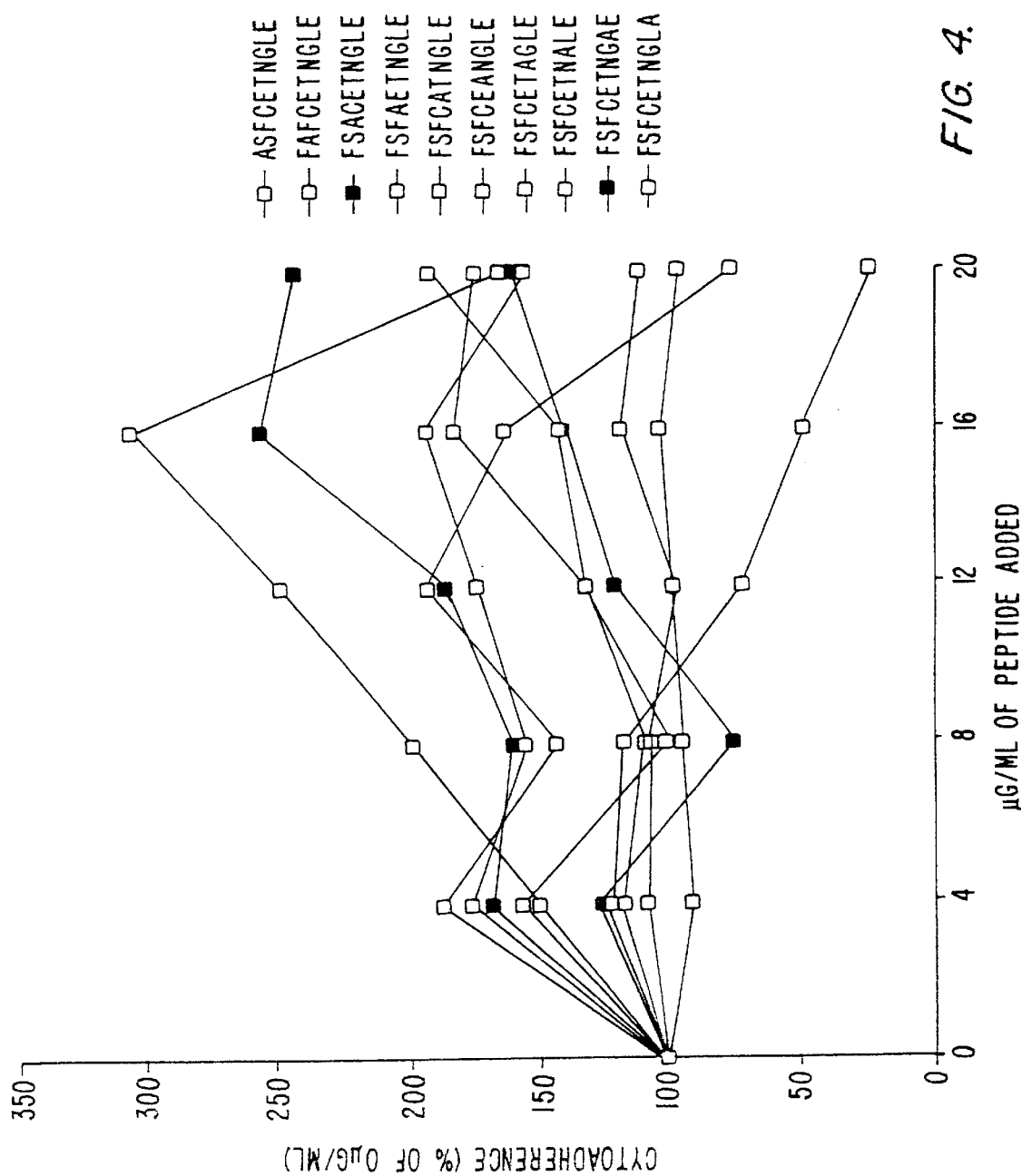
FIG. 4 illustrates the results of cytoadherence inhibition assays using peptides SEQ ID NOS:29–38.

The mechanism by which 5H12 inhibited pfalhesin/ erythrocyte interactions but not pfalhesin/C32 amelanotic melanoma interactions was not immediately obvious. In order to determine if the action of the antibody was due to the non-competitive removal of the sequence FSFCETNG-LEYI [SEQ ID NO:44], the antibody's epitope, or whether it was the result of steric hindrance or induced conformational change of the protein associated with the antibody's binding, the effect of adding increased amounts of the peptide FSFCETNGLE [SEQ ID NO:26] to rosetting and cytoadherence assays was determined. Addition of the peptide FSFCETNGLE [SEQ ID NO:26] resulted in competitive inhibition of cytoadherence and rosetting (FIGS. 3A and 3B) with $IC_{50}$ values of 4 µM and 3 µM. FIG. 3A illustrates the results of adding the indicated peptides to the incubation medium of a cytoadherence assay. The Y axis in FIG. 3A indicates percentage of control adherence (where 0 µg/ml peptide added is taken as 100%). Attempts to produce a scrambled version of the peptide to act as a negative control resulted in at less active and an inactive peptide. FIG. 3B illustrates the results of adding the peptide FSFCETNGLE [SEQ ID NO:26] to the incubation medium of a rosetting assay; the Y axis indicates actual number of uninfected erythrocytes per infected erythrocyte, and the results are the average of duplicate determinations with actual values shown by bars. These results suggest that the human band 3 protein may contain a region that is capable of mimicking CD36.

To determine whether the Mab 5H12 could cross react with CD36 attempts were made to stain cells expressing CD36 on their surface. The CD36-like region was found to be antigenically distinct from CD36, since the Mab 5H12 did not stain C32 amelanotic melanoma cells or CHO cells transfected with the CD36 gene.

The observation that the human band 3 protein contains a potential CD36 adhesin and a potential CD36-like receptor suggested that intermolecular (resulting in dimers or tetramers) or intramolecular (contributing to the protein's tertiary structure) interactions might be taking place. To determine if the adhesin/receptor pair contributed to intermolecular interactions the effect of increasing amounts of the peptide on the distribution of monomers, dimers and tetramers was determined. No effect of the peptide on the polymeric state of band 3 was observed.

Based upon the foregoing, it appears that CD36 mediated cytoadherence results from the interaction of CD36 on target cells and pfalhesin present on the surface of *P. falciparum*-infected erythrocytes. CD36 mediated rosetting appears to be the result of an intercellular interaction between two distinct regions of the human band 3 protein. This conclusion is based on the observations that a monoclonal antibody, 5H12, is capable of selectively interfering with rosetting (and thereby promotes the competing process of cytoadherence), and that a synthetic peptide based on the amino acid sequence of 5H12's epitope (present in the band 3 protein) can competitively inhibit both cytoadherence and rosetting with approximately equal $IC_{50}$ values (4 µM and 3 µM).

The epitope of the Mab 5H12 consists of the amino acid sequence FSFCETNGLE [SEQ ID NO:26]. Indirect experimental evidence and the results of alanine substitution for individual residues in pfalhesin suggest that the active residues in the peptide are the tyrosine, the lysine and the histidine (when the histidine is protonated). Examination of the sequence FSFCETNGLE [SEQ ID NO:26] suggests that it contains a region with the potential to interact with a tyrosine (FSF) with a single amino acid separating it from a negatively charged residue, glutamic acid (E), followed by four amino acids and another glutamic acid residue (FxFxExxxxE [SEQ ID NO:49]). Two attempts were made to construct an inactive scramble of the active sequence. The first attempt, FETLGCNEGF [SEQ ID NO:27], resulted in a peptide with diminished activity, possibly due to the presence of negatively charged residues and a phenylalanine residue forming the pattern FExxxxxExF (SEQ ID NO:50), which might be able to exist in a conformation that mimics the active peptide. The second attempt at a scramble, FFS-ATLGNEE [[SEQ ID NO:28], was inactive because the phenylalanine residues and the glutamic acid residues were clustered at opposite ends of the peptide.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A substantially pure peptide of 10 to 50 amino acids in length comprising a sequence selected from the group consisting of FSFCETNGLE (SEQ ID NO:26), ASFCETNGLE (SEQ ID NO:29), FAFCETNGLE (SEQ ID NO:30), FSACETNGLE (SEQ ID NO:31), FSFAETNGLE (SEQ ID NO:32), FSFCEANGLE (SEQ ID NO:34), FSFCETAGLE (SEQ ID NO:35), FSFCETNALE (SEQ ID NO:36) and FSFCETNGAE (SEQ ID NO:37).

2. A peptide according to claim 1, having a sequence FSFCETNGLE [SEQ ID NO:26].

3. A peptide according to claim 1, wherein the peptide comprises D-amino acids.

4. A composition for reducing adhesiveness of red blood cells in a mammalian patient characterized by a condition selected from the group consisting of *P. falciparum* infection, sickle cell disease, thalassemia and diabetes, said composition comprising a suitable carrier or adjuvant and an amount effective to reduce adhesiveness of red blood cells of at least one peptide of 10 to 50 amino acids in length, wherein the peptide comprises a sequence selected from the group consisting of FSFCETNGLE (SEQ ID NO:26), ASFCETNGLE (SEQ ID NO:29), FAFCETNGLE (SEQ ID NO:30), FSACETNGLE (SEQ ID NO:31), FSFAETNGLE (SEQ ID NO:32), FSFCEANGLE (SEQ ID NO:34), FSFCETAGLE (SEQ ID NO:35), FSFCETNALE (SEQ ID NO:36) and FSFCETNGAE (SEQ ID NO:37).

5. A composition according to claim 4, wherein the peptide has a sequence FSFCETNGLE [SEQ ID NO:26].

6. A composition according to claim 4, wherein the peptide comprises D-amino acids.

* * * * *